US009538955B2

(12) United States Patent
De Waele et al.

(10) Patent No.: US 9,538,955 B2
(45) Date of Patent: Jan. 10, 2017

(54) METHOD AND APPARATUS FOR DETERMINING ANATOMIC PROPERTIES OF A PATIENT

(71) Applicant: KONINKLIJKE PHILIPS N.V., Eindhoven (NL)

(72) Inventors: Stijn De Waele, Millwood, NY (US); Adrienne Heinrich, Den Bosch (NL); Frederik Jan De Bruijn, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 212 days.

(21) Appl. No.: 14/353,104

(22) PCT Filed: Oct. 9, 2012

(86) PCT No.: PCT/IB2012/055443
§ 371 (c)(1),
(2) Date: Apr. 21, 2014

(87) PCT Pub. No.: WO2013/057627
PCT Pub. Date: Apr. 25, 2013

(65) Prior Publication Data
US 2014/0288463 A1    Sep. 25, 2014

Related U.S. Application Data

(60) Provisional application No. 61/549,923, filed on Oct. 21, 2011.

(51) Int. Cl.
| G01B 11/30 | (2006.01) |
| A61B 5/00 | (2006.01) |
| A61B 5/107 | (2006.01) |

(52) U.S. Cl.
CPC ........... *A61B 5/4818* (2013.01); *A61B 5/1076* (2013.01); *A61B 5/1079* (2013.01); *A61B 5/4542* (2013.01); *G01B 11/30* (2013.01)

(58) Field of Classification Search
CPC ........... G01N 2035/00326; G01N 2035/00495; G01N 1/02; G01N 2001/027; G01N 2001/028; G01N 2035/00277; G01N 2035/00564; G01N 21/78; G01N 2458/30; G01N 27/28; G01N 27/3271; G01N 27/3272; G01N 27/3273
See application file for complete search history.

(56) References Cited

U.S. PATENT DOCUMENTS

| 6,144,453 A | 11/2000 | Hallerman et al. |
| 6,549,288 B1 | 4/2003 | Migdal et al. |

(Continued)

FOREIGN PATENT DOCUMENTS

| EP | 1767897 A1 | 3/2007 |
| JP | 2002250613 A | 9/2002 |

(Continued)

OTHER PUBLICATIONS

Thulesius et al, "Pharyngometric Correlations With Obstructive Sleep Apnea Syndrome", Acta Oto-Laryngologica, vol. 124, No. 10, 2004, p. 1182-1186.

(Continued)

*Primary Examiner* — Michael P Stafira

(57) ABSTRACT

A method is disclosed for determining anatomical properties of a patient, the patient having an oral cavity and a throat, comprising a) projecting at least one structured light pattern into the patient's oral cavity; b) detecting at least one reflected light pattern, each of the reflected light patterns emanating from reflection of a corresponding projected structured light pattern; c) analysing the at least one reflected structured light pattern in view of the at least one structured light pattern, thereby determining anatomical properties of the patient; and an associated imaging device.

13 Claims, 6 Drawing Sheets

(56) References Cited

U.S. PATENT DOCUMENTS

| | | | |
|---|---|---|---|
| 7,312,924 B2 | 12/2007 | Trissel | |
| 7,672,504 B2 | 3/2010 | Childers | |
| 7,813,591 B2 | 10/2010 | Paley et al. | |
| 2003/0164952 A1 | 9/2003 | Deichmann et al. | |
| 2006/0093206 A1* | 5/2006 | Rubbert | G01B 11/2513 |
| | | | 382/154 |
| 2007/0172112 A1 | 7/2007 | Paley et al. | |
| 2009/0221874 A1 | 9/2009 | Vinther et al. | |
| 2010/0149315 A1* | 6/2010 | Qu | A61B 1/00193 |
| | | | 348/46 |
| 2010/0311005 A1 | 12/2010 | Liang | |
| 2012/0062716 A1* | 3/2012 | Dillon | A61C 9/006 |
| | | | 348/66 |
| 2013/0027515 A1* | 1/2013 | Vinther | A61B 1/00177 |
| | | | 348/44 |

FOREIGN PATENT DOCUMENTS

| | | |
|---|---|---|
| JP | 20008119305 A | 5/2008 |
| JP | 2009165558 A | 7/2009 |
| JP | 2010279695 A | 12/2010 |
| WO | WO2007059780 | 5/2007 |
| WO | WO2010145669 | 12/2010 |

OTHER PUBLICATIONS

M.K. Erman et al., Validation of the ApneaLink for the Screening of Sleep Apnea: A Novel and Simple Single-Channel Recording Device, Journal of Clinical Sleep Medicine, vol. 3, No. 4, 2007, pp. 387-392.

M. Friedman et al., "Clinical Predictors of Obstructive Sleep Apnea", The Laryngoscope, Dec. 1999 The American Laryngological Rhinological and Otological Society, Inc., pp. 1901-1907.

M. Friedman et al., "Clinical Staging for Sleep-Disordered Breathing", Otolaryngology—Head and neck Surgery, Jul. 2002, vol. 127, No. 1, pp. 13-21.

C.D. Gray, "Acoustic Pulse Reflectometry for Measurement of the Vocal Tract with Application in Voice Synthesis", The University of Edinburgh, (A thesis submitted in fulfilment of the requirements for the degree of Doctor of Philosophy to the University of Edinburgh 2005), pp. 1-252.

D. Gun Jung et al., "Predictive Value of Kushida Index and Acoustic Pharyngometry for the Evaluation of Upper Airway in Subjects With or Without Obstructive Sleep Apnea", J Korean Med Sci 2004; 19; pp. 662-667.

R.W.W. Lee et al., "Craniofacial Phenotyping in Obstructive Sleep Apnea—A Novel Quantitative Photographic Approach", SLEEP, vol. 32, No. 1, 2009, pp. 37-45.

G. Liistro et al., "High Mallampati Score and Nasal Obstruction are Associated Risk Factors for Obstructive Sleep Apnoea", Eur Respir J 2003; 21: pp. 248-252.

J. MacQueen, "Some Methods for Classification and Analysis of Multivariate Observations", Proceedings of 5th Berkeley Symposium on Mathematical Statistics and Probability, University of California Press, 1967, pp. 281-297.

J. Salvi et al., Pattern Codification Strategies in Structured Light Systems, Pattern Recognition, vol. 37, Issue 4, Apr. 2004, pp. 827-849.

X. Zhao et al., "Three-Dimensional Upper-Airway Changes Associated with Various Amounts of Mandibular Advancement in Awake Apnea Patients", American Journal of Orthodontics and Dentofacial Orthopedics, May 2008, vol. 133, No. 5, pp. 661-668.

\* cited by examiner

METHOD AND APPARATUS FOR DETERMINING ANATOMIC PROPERTIES OF A PATIENT

CROSS-REFERENCE TO PRIOR APPLICATIONS

This application is the U.S. National Phase application under 35 U.S.C. §371 of International Application Ser. No. PCT/IB2012/055443, filed on Oct. 9, 2012, which claims the benefit of United States Application Serial No. 61/549,923, filed on Oct. 21, 2011. These applications are hereby incorporated by reference herein.

FIELD OF THE INVENTION

The present invention relates to the field of methods and apparatuses for determining anatomic properties of a patient. More specifically it relates to determining internal anatomic properties of a patients oral cavity and throat. The present invention can advantageously be applied in the field of screening for obstructive sleep apnea and related medical cases.

BACKGROUND OF THE INVENTION

Convenient and accurate measurement of throat anatomy is relevant for daytime screening for obstructive sleep apnea (OSA). Obstructive sleep apnea is a medical condition wherein the upper respiratory tract is blocked by features within the oral cavity of throat of the patient, preventing a patient from breathing normally, especially when sleeping.

Today, patients exhibiting OSA symptoms need to be monitored during their sleep, and need to go to a sleep lab. This is very tedious and labour-intensive. Obviously, more comfortable and less time-consuming approaches are needed.

Alternative practices which may indicate the presence of OSA with a patient, without sleep lab, are still not accurate enough and cannot sufficiently be trusted. Visual methods include classifying the ensemble of oral cavity and throat in categories (e.g. by using Mallampati scores, see FIG. 1(a), or tonsil grade scores, see FIG. 1(b)) by visual inspection by a human expert. Obviously this implies subjective interpretation and low reproducibility. A follow-up in time of the specific patient's evolution is difficult, and different human experts may categorise the same patient differently.

Another alterative practice comprises the use of a pharyngometer, which is based on an acoustic scanning of the nasal or oral cavity. A good acoustic seal is required for an accurate measurement, which is difficult to achieve. Acoustic scanning provides only little information on the anatomy. Advanced 3D imaging techniques as for instance MRI are expensive and are only available in hospitals, whereas OSA screening typically takes place in the office a primary health physician.

A camera has been used to measure craniofacial anatomic features related to OSA, in "Craniofacial Phenotyping in Obstructive Sleep Apnea—A Novel Quantitative Photographic Approach", Richard W. W. Lee et al., published in SLEEP, Vol. 32, No. 1, 2009. Parameters relating to craniofacial morphology are derived from frontal-profile photographs of patients.

SUMMARY OF THE INVENTION

It is an object of the present invention to provide for determining anatomical properties of a patient's throat and oral cavity, which is quick, easy and significantly precise in order to screen a patient's condition with respect to sleep apnea.

The above objective is accomplished by a method and device according to the present invention.

Particular and preferred aspects of the invention are set out in the accompanying independent and dependent claims. Features from the dependent claims may be combined with features of the independent claims and with features of other dependent claims as appropriate and not merely as explicitly set out in the claims.

According to a first aspect of the present invention, a method for determining internal anatomical properties of a patient is disclosed, the patient having an oral cavity and a throat, comprising
  projecting at least one structured light pattern into the patient's oral cavity;
  detecting at least one reflected light pattern, each of the reflected light patterns emanating from reflection of a corresponding projected structured light pattern;
  analysing the at least one reflected structured light pattern in view of the at least one structured light pattern, thereby determining anatomical properties of the patient.

It is an advantage of aspects of the present invention that detailed information about internal anatomical properties of the patient oral cavity and throat can be derived in an objective, reproducible way.

According to preferred embodiments of the present invention, one structured light pattern is projected, one reflected light pattern is detected, and the analysis is based thereon.

According to other preferred embodiments of the present invention, a plurality of, typically different, structured light patterns is projected sequentially, and a plurality of associated reflected light patterns is detected sequentially. The analysis can then be based on the plurality of structured light patterns and associated reflected light patterns. Using a plurality of different structured light patterns may increase the efficiency of the method as it may reduce the likelihood of erroneous identification of anatomical properties and thus anatomical features of the patient's mouth.

According to preferred embodiments, the detection of reflected structured light patterns is synchronised with the breathing cycle of the patient. For instance, reflected light patterns can be detected when the patient is breathing in, thereby deriving the anatomical properties of the patient in a first state. Also, reflected light patterns can be detected when the patient is breathing out, thereby deriving anatomical properties of the patent in a second state. Afterwards the anatomical properties in the first state and in the second state can be compared. This for instance in order to derive information as to whether a patient suffers from sleep apnea (and/or to which extent) or not.

Note that according to the present invention, detecting reflected light (patterns) may also comprise filming or video recording said reflected light patterns. A photograph can correspond to a particular image corresponding to the video image at a predetermined moment in time.

According to preferred embodiments of the present invention, the method further comprises the use of one or more polarisation filters.

The method may comprise polarising the reflected light patterns before detection, for instance by having the reflected light patterns passing through one or more polarisation filters.

The method may comprise polarising the structured light patterns before reflection, according to a first polarisation mode, and polarising the reflected light patterns before detection and after reflection, according to a second polarisation mode, the first and second polarisation modes being opposite, e.g. horizontal and vertical, or left circular and right circular. This can for instance be achieved by using a set of two polarisation filters, whereby the light projected light patterns are passing through one of the polarisation filters before reflection, and through the second polarisation filter after reflection and before detection. A first filter can then be placed in between the projector and the oral cavity, a second filter in between the oral cavity and the detector.

These embodiments provide the advantage that images of specular reflections of light in the on saliva can be suppressed in the detected reflected pattern. The presence of such reflections may negatively impact the analysis step and could reduce the quality of the determination of the internal anatomic properties of the patient.

According to preferred embodiments of the present invention a baseline between a location of projecting at least one structured light pattern and a location of detecting at least one reflected light pattern, is smaller than 7 cm, or smaller than 6 cm, or smaller than 5 cm, or smaller than 4 cm, or smaller than 3 cm, or smaller than 2 cm, or even smaller than 1 cm. It can be about 7 cm, 6 cm, 5 cm, 4 cm, 3 cm, 2 cm, 1 cm or smaller. It can be within the range of 0.5-10 cm, more preferably within the range of 1-7 cm.

The fact that internal anatomical properties are retrieved of the patient oral cavity and/or throat, means in practice that the projector and detector should be placed within close distance of the mouth, or, according to certain embodiments, within the mouth of the patient. Note that theoretically a projector and detector cannot be placed on exactly the same location as this would not allow extraction of appropriate information and thus properties. This means though that the baseline of the system can be relatively small. The baseline can be small enough in order for the detector and projector to be integrated in a patient interfacing device which is adapted for being inserted into the patient's mouth. Moreover, according to certain embodiments, projector and detector can be integrated in a pharyngeal endoscope, which is adapted for being inserted in the patient's mouth.

According to preferred embodiments of the present invention, the patient comprises a tongue, and the method further comprises depressing the tongue, for instance by means of a spatula, while projecting the at least one structured light pattern into the patient's oral cavity.

This provides the advantage that the method can be performed in an even more substantially reproducible way, because the imaging device can be positioned in a substantially reproducible way for a certain patient. Another advantage is that the imaging system can be used in more or less the same angle/distance for different patients; the tongue's location is not substantially variable between patients.

According to preferred embodiments of the present invention each of the at least one structured light pattern comprises a set of predetermined parallel lines.

The lines of at least one, or all, structured light patterns can for instance be straight or curved.

The parallel lines of at least one, or all, structured line pattern(s) can have constant width. The width of the lines can for instance be smaller than 5 mm, or smaller than 4 mm, or smaller than 3 mm, or smaller than 2 mm, or smaller than 1 mm. It can for instance be equal to 5 mm or 4 mm or 3 mm or 2 mm or 1 mm.

The parallel lines of at least one, or all, structured light pattern(s) can be positioned at constant or non-constant distances from neighbouring parallel lines.

The parallel lines of at least one, or all, structured light patterns can for instance be forming concentric circles.

According to preferred embodiments of the present invention the at least one structured light pattern is predetermined such that the set of parallel lines defines a structure comprising higher line density areas and lower line density areas, the projections thereof corresponding with predetermined locations in the oral cavity and throat. These predetermined locations can for instance correspond to locations where respectively relatively smaller structures (higher density) and relatively larger structures (lower density) are expected. Whether, which and where structures are expected in a patient's mouth may be determined based on statistics, standard models or other means.

According to preferred embodiments of the present invention the at least one structured light pattern is predetermined such that the set of parallel lines defines a structure comprising larger line thickness areas and smaller line thickness areas, the projections thereof corresponding with predetermined locations in the oral cavity and throat where respectively larger structures and smaller structures are expected.

Both of the above embodiments, on themselves or in combination (included as a separate embodiment), provide the advantage that the analysis can be performed more accurately, i.e. they result in an even more efficient method. Using predetermined information comprising as to where specific features of the oral cavity and/or mouth and/or throat are expected relative to the oral cavity, allows the determination of further optimised structured light patterns for the specific application to which the method pertains Thinner lines and larger line densities allow the extraction of more detailed information, but may increase required processing power. Processing power can thus be reduced by using higher line density and/or thinner lines only where such detailed information is valuable, ie where certain anatomical features can be expected.

According to preferred embodiments of the present invention detecting the at least one reflected structured light pattern comprises making one or more photographic image(s) of the patient's oral cavity.

According to preferred embodiments of the present invention, the method further comprises making at least one photographic reference image of the patient's oral cavity when no projection of the structured light pattern is being made, and analysing the at least one reflected light pattern further comprises subtracting a/the respective photographic reference image(s) from the respective photographic image(s). A single photographic reference image can be used for a plurality of detected light patterns, or a plurality of different photographic reference images corresponding to respective detected light patterns from said plurality of detected light patterns. Note that a photographic image can be the image of a video stream at a certain moment in time.

These embodiments typically provide the advantage that respective elaborated images result, mainly or only comprising projected patterns. This can simplify analysis and information extraction further.

According to preferred embodiments of the present invention, the method further comprises detecting fractures or interruptions in reflected lines of reflected light patterns and associating the fractures or interruptions with boundaries of internal anatomic features of the oral cavity.

According to preferred embodiments of the present invention, the method further comprises detecting deformation of reflected lines of respective projected light patterns and associating the deformations with shape information of internal anatomic features of the oral cavity. Shape information can comprise 2D shape information or 3D shape information.

According to preferred embodiments of the present invention, determining internal anatomic properties of the patient comprises determining an extent to which the back of the throat is occluded by other anatomical features forming the oral cavity or within the oral cavity. The other anatomical features can for instance be one or more of the following: the velum, hard palate, tongue, tonsils, uvula, teeth, but other features may also be present and may occlude the throat.

According to preferred embodiments of the present invention, determining an extent to which the back of the throat is occluded by other anatomical features forming the oral cavity or within the oral cavity comprises:

imaging the patient's oral cavity, throat and mouth;
determining the contour of the mouth;
determining the surface area of the visible part of the throat wall;
normalising the surface area of the visible part of the throat wall with the total mouth area, the total mouth area being determined based on the contour of the mouth.

Determining the visible surface area of the throat wall can for instance comprise:

using an image segmentation algorithm to segment the image for the mouth area, the mouth area being defined by the contour of the mouth;
determining a number of segments by splitting the mouth area in two to five segments and selecting the optimal number of segments based on a goodness of fit, based on the number of expected anatomical features in the oral cavity and throat; when the selected number of segments is larger than two, identifying the middle segment(s) as the segment(s) of the visible part of the throat wall (when it is equal to or smaller than two, the method should be repeated);
determine the surface area of the segment(s) identified as corresponding to the visible part of the throat wall.

When the projection, and therefor also detection, of structured light patterns is performed within the mouth, for instance by means of a integrated device comprising a projector and a detector, normalising by the total mouth area is not necessarily applicable (if it is applicable, a independent determination of the mouth area should be performed, base on an an external image) and can be omitted.

The method can then comprise:
imaging the patient's oral cavity and throat;
determining the surface area of the visible part of the throat wall;
Determining the surface area of the visible part of the throat wall can comprise;

using an image segmentation algorithm to segment the image;
determining a number of segments by splitting the imaged area in two to five segments and selecting the optimal number of segments based on a goodness of fit, based on the number of expected anatomical features which has been imaged in the oral cavity and throat; when the selected number of segments is larger than two, identifying the middle segment(s) as the segment(s) of the visible part of the throat wall (when it is equal to or smaller than two, the method should be repeated);
determine the surface area of the identified segment(s) of the visible part of the throat wall.

The surface area of the identified throat wall segments can for instance be used as a parameter in order to determine whether a patient is suffering from sleep apnea.

According to preferred embodiments of the present invention, deriving the internal anatomical properties of the patient comprises deriving depth information for internal anatomic features within the oral cavity or throat. Depth information is information which indicates how far an object in an image of a 3D scene is separated from the detector (camera).

According to a second aspect of the present invention, an imaging device for determining internal anatomical properties of a patient is disclosed, the patient having an oral cavity and a throat, comprising a means for projecting at least one structured light pattern into the patient's oral cavity, for instance a projector;
a means for detecting at least one reflected light pattern, each of the reflected light patterns emanating from reflection of a corresponding projected structured light pattern, for instance a detector;
a means for analysing the at least one reflected structured light pattern in view of the at least one structured light pattern, thereby determining internal anatomical properties of the patient, for instance an analysing device, for instance a computer comprising a software for performing such analysing.

According to preferred embodiments of the present invention, the imaging device further comprises a first polarising means for polarising the structured light patterns before reflection, according to a first polarisation mode, and a second polarising means for polarising the reflected light patterns before detection and after reflection, according to a second polarisation mode, the first and second polarisation modes being opposite. The first and second polarisation means can be polarisation filters as described for the first aspect. A first filter can then be located in between the projector and the oral cavity, a second filter can be located in between the oral cavity and the detector.

According to preferred embodiments, projection means (projector), detection means (detector) and one or more polarisation filters may be comprised in a common housing; especially when comprised in an imaging device adapted for being inserted in a patient's mouth.

According to preferred embodiments of the present invention, a baseline between the projector and the position of the detector, is 7 cm, or smaller than 6 cm, or smaller than 5 cm, or smaller than 4 cm, or smaller than 3 cm, or smaller than 2 cm, or even smaller than 1 cm. It can be about 7 cm, 6 cm, 5 cm, 4 cm, 3 cm, 2 cm, 1 cm or smaller.

According to preferred embodiments of the present invention, the imaging device further comprises a means for depressing the tongue of a patient, for instance a spatula or other device which is suitable for it.

According to preferred embodiments of the present invention, the imaging device is adapted for projecting a structured light pattern comprising a set of predetermined parallel lines.

According to preferred embodiments of the present invention, the imaging device is adapted for projecting a structured light pattern comprising higher line density areas and lower line density areas, the projections thereof corresponding with predetermined locations in the oral cavity and throat.

According to preferred embodiments of the present invention, the imaging device is adapted for projecting a structured light pattern comprising larger line thickness areas and smaller line thickness areas, the projections thereof corresponding with predetermined locations in the oral cavity and throat.

According to preferred embodiments of the present invention, the means for analysing is adapted for detecting fractures in reflected lines of reflected light patterns, and associating the fractures with boundaries of anatomic features of the oral cavity.

According to preferred embodiments of the present invention, the means for analysing is adapted for detecting deformation of reflected lines of reflected light patterns, and associating the deformation with shape information of anatomic features of the oral cavity.

According to preferred embodiments of the present invention, the means for analysing is adapted for determining an extent to which the back of the throat is occluded by other anatomical features forming the oral cavity or within the oral cavity.

According to preferred embodiments of the present invention, the means for analysing is adapted for determining depth information for anatomic features within the oral cavity or throat.

According to a third aspect of the present invention, the use of patterned light projection and detection techniques for retrieving anatomic properties of the oral cavity and throat of a patient is disclosed.

In the above, features and advantages corresponding to embodiments of the first aspect of the present invention are supposed to be also disclosed, mutatis mutandis, for the second aspect of the present invention, and vice versa.

The teachings of the present invention permit the design of improved methods and apparatus for identifying internal features of a patient, and to thereby identify whether and to which extent a patient suffers from sleep apnea.

BRIEF DESCRIPTION OF THE DRAWINGS

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

Figure 1:
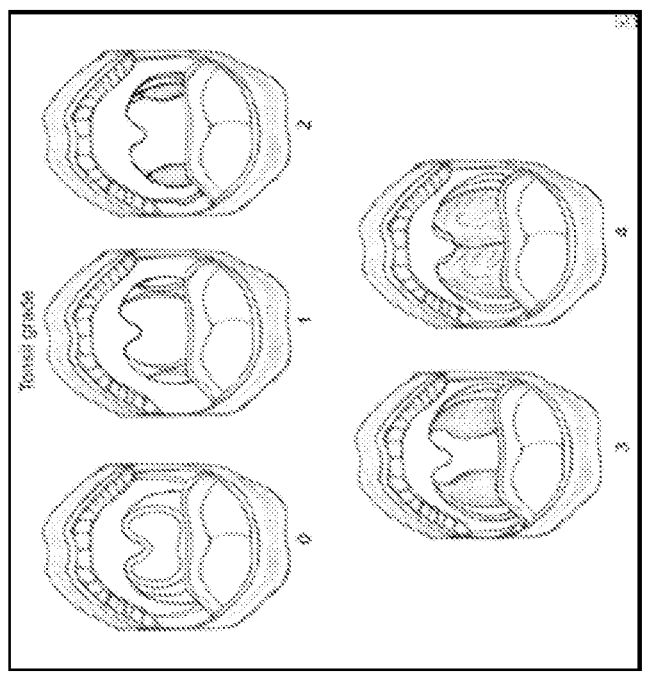
FIGS. 1(a) and (b) illustrate the state of the art Mallampati score and tonsil grade score respectively. They are established by visual inspection when screening for OSA. They require trained personnel, and even then are difficult to measure in a repeatable way.
Figure 1:
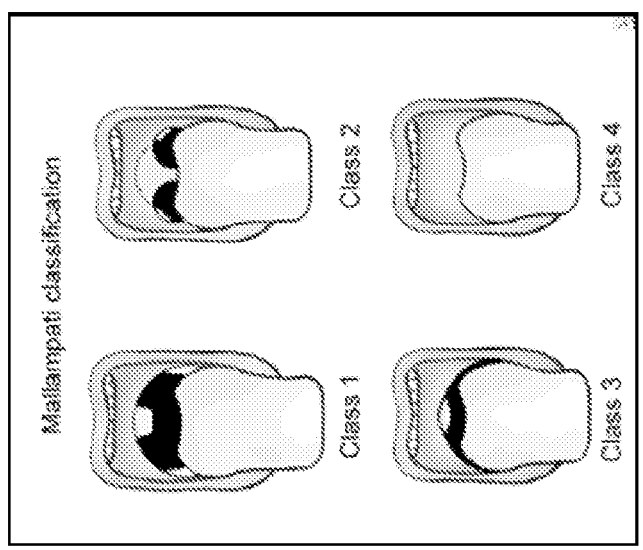

In the different figures, the same reference signs refer to the same or analogous elements.

DETAILED DESCRIPTION OF THE EMBODIMENTS

The present invention will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes.

Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

Furthermore, the terms first, second, third and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

Furthermore, some of the embodiments are described herein as a method or combination of elements of a method that can be implemented by a processor of a computer system or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the invention.

In the description provided herein, numerous specific details are set forth. However, it is understood that embodiments of the invention may be practiced without these specific details. In other instances, well-known methods, structures and techniques have not been shown in detail in order not to obscure an understanding of this description.

The following terms or definitions are provided solely to aid in the understanding aspects of the invention:
  anatomical properties of the oral cavity or throat of a patient refers to surface area, sub surface area, and sub surface orientation of the surface of the oral cavity and throat of the patient;
  anatomical features of the oral cavity of a patient refers to identified specific portions of the oral cavity or throat, as for instance tongue, tonsils, ubula, back wall of the throat;
  the baseline is the distance between a means for projecting such as a projector and a means for detecting such as a photographic camera; it is also the distance between a location of projecting and a location of detecting.
  a structured light pattern is a predetermined known, non uniform, pattern of light. The pattern often comprises often grids or parallel stripes, but many other patterns of structured light are possible, as is known by the skilled person. When such a structured pattern is projected onto a scene, seen from other perspectives then from the projector, the pattern appears geometrically distorted. The way that these deform when striking surfaces allows vision systems to calculate the depth and surface information of the objects in the scene.

Aspects of the invention relate to methods and devices for determining internal anatomical properties of a patient's throat, suitable for screening for Obstructive Sleep Apnea.

Therefor a method is described (and corresponding device) comprising
  projecting one structured light pattern or a sequence of at least one structured light patterns (so-called structured light) into a patient's oral cavity and/or throat;
  detecting reflected light emanating from a patient's oral cavity and/or throat in response to projecting the one or more light pattern;
  analyzing the reflected structured light pattern in view of the at least one structured light patterns, thereby determining internal anatomical properties of the patient.

Aspects of the present invention apply computational imaging to measure properties of the throat anatomy and use these properties for OSA screening.

In a first family of embodiments, the areas investigated by the Mallampati score (black areas in FIG. 1(a)) are derived. These measures are illustrative of how severely the back of the throat is occluded, e.g. by the velum, hard palate, tonsils and tongue. By determining these measures, a degree of suffering of sleep apnea can be determined for a patient.

In a second family of embodiments, a depth map of the mouth and throat is rendered.

In both families, a pattern is projected into the mouth which deflects at the boundaries of the anatomical entities or features.

For OSA screening, aspects of the present invention add information on the throat anatomy that can improve screening performance.

Figure 2:
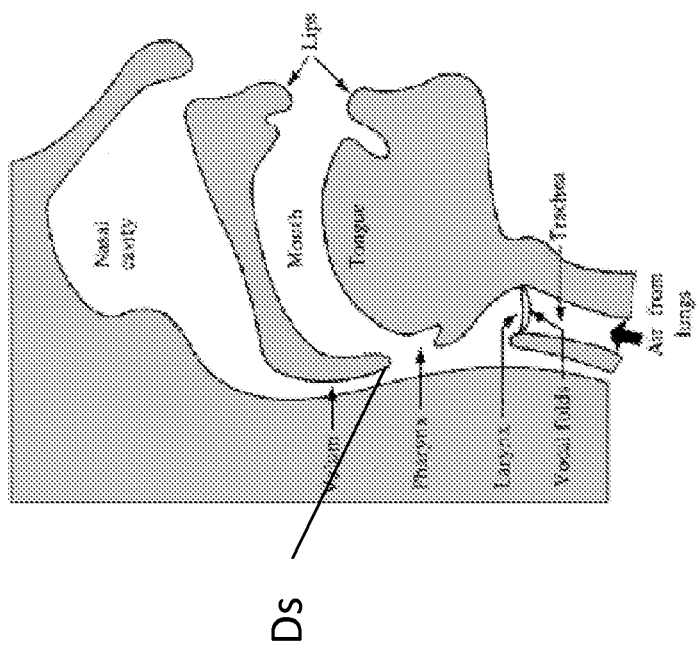
FIG. 2 illustrates a mid-sagittal profile showing the principal features of the voice organ. The saggital diameter of the velopharynx is indicated in by "Sd".

A specific example is to use the obtained 3D information to get an estimate for the saggital diameter Ds and/or area of the velopharynx (illustrated in relation with FIG. 2).

According to preferred embodiments of the present invention, the areas of the velum, the tonsils, the hard palate and the back of the throat, and the saggital diameter of the velopharynx are determined and used. First a structured light pattern is projected into the throat of the patient, in such a way that both the velum and the throat wall behind it are visibly lit by the pattern. A dense line pattern is preferred for better distinguishing the different anatomical boundaries and objects. One or more images is/are measured using a standard camera and a processing unit which can for instance be embedded with the camera. Then, computational imaging and computer vision techniques are used to identify the velum and to extract the distance from the velum to the back of the throat.

According to an embodiment according to the first family, typically requiring a less complex implementation, the areas investigated by the Mallampati score are measured. This approach takes advantage of the smooth surfaces of anatomical objects in the mouth. A line pattern is projected into the mouth of a patient as shown in FIG. 3(a).

It is visible that the lines keep their orientation and alignment as long as they are projected over areas within one anatomical object. When crossing anatomical boundaries, the lines deflect and their orientation changes. Also a shift in space occurs (see line break between the palate and throat wall). This can be automatically analyzed with e.g. an edge detector, rendering the boundaries of the projected lines (see FIG. 3(b)). The boundaries of the lines can then be analyzed according to the following parameters:
  orientation of the lines;
  extension of lines;
  interruption or fractures of lines.

Lines with the same orientation belong to the same area, their extension or length can be used to estimate the anatomical area they are covering (and its corresponding surface value).

Figure 3:
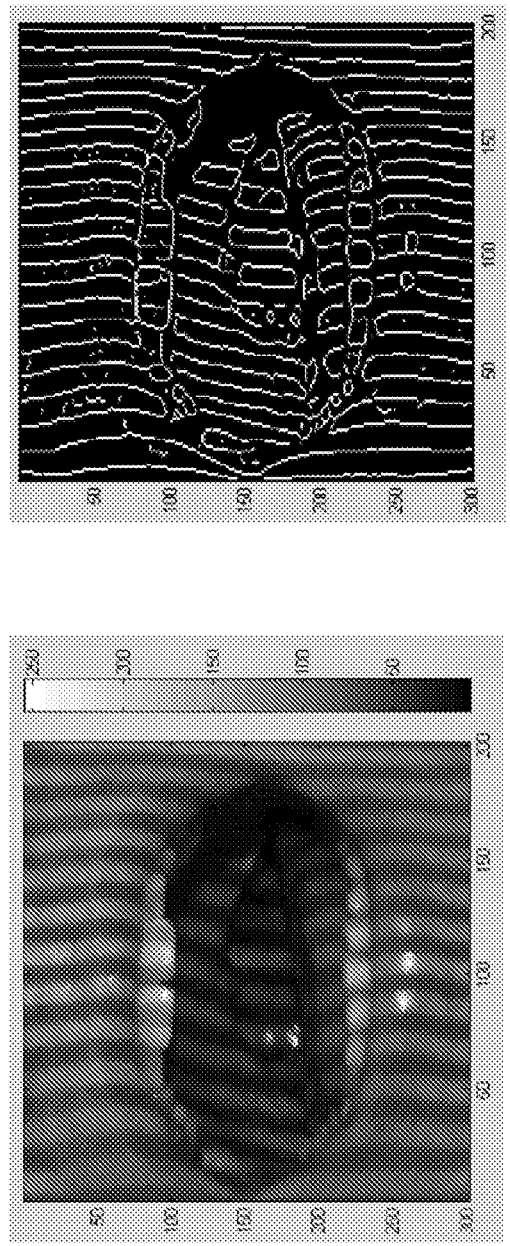
FIG. 3(a) illustrate a line pattern being projected into the mouth of a patient. A canny edge detector renders the boundaries of the projected lines, illustrated in FIG. 3(b).

According to certain embodiments, also denser and thinner lines can be used than the ones employed in FIG. 3(a) for a good estimate of the areas in the mouth, particularly the tonsils, the throat wall and the velum. This approach can be extended by illuminating only every other image with the pattern. The intermediate images (reference images) can be subtracted from the images with pattern, which results in images where only the pattern is visible (see FIG. 3(b)). This will make the analysis of the lines easier, and thus comprises preferably additional pattern projection control. According to a further improvement a polarization filter is included, e.g. having the reflected structured light patterns passing through a polarization filter, to reduce the effects of glare on the images. A set of two polarisation filters can also be used, as described before.

An objective version of the Mallampati score can for instance be defined as the area of the visible part of the throat wall, according to the following method:

1) determining the contour of the mouth by detecting the transition between skin color and mouth color;
2) using an image segmentation algorithm to segment the image for the area containing the mouth. For instance by using both color information and projected light information. Using color information, pixels are combined by similarity in color value e.g. using the K-means algorithm (see for instance J. B. MacQueen (1967). "Some Methods for classification and Analysis of Multivariate Observations". Proceedings of 5th Berkeley Symposium on Mathematical Statistics and Probability. University of California Press. pp. 281297. MR0214227. Zb10214.46201. The projected light information is used by clustering pixels where the pattern gradient direction is similar;
3) The number of segments is then determined by splitting the mouth area in 2 to 5 segments and selecting the optimal number of segments based on a goodness of fit. The considered number of segments is determined by the number of expected anatomical features in the mouth;
4) Identifying the middle segment(s) as the segment(s) of the throat wall, when the number of segments exceeds 2 (hereby, the throat wall is considered to be visible). Optionally, a step of verifying correctness of the selected segments can be included, such a step comprising asking user input and making adjustments if needed;
5) Calculating the area if of the selected throat wall segments(s);
6) Normalising the area of the selected throat wall with the total mouth area.

As discussed, when the projection, and therefor also detection, of structured light patterns is performed within the mouth, for instance by means of a integrated device comprising a projector and a detector, normalising by the total mouth area is not necessarily applicable (if it is applicable, an independent determination of the mouth area should be performed, base on an external image) and can be omitted.

The method can then comprise:
imaging part of the patient's oral cavity and throat;
using an image segmentation algorithm to segment the image;
determining a number of segments by splitting the imaged area in two to five segments and selecting the optimal number of segments based on a goodness of fit, based on the number of expected anatomical features which has been imaged in the oral cavity and throat. The maximum number of five segments can be based on the number of expected anatomical features in the oral cavity and throat. For each number of segments n=1, 2, 3, 4, 5, the image can be approximated by a constant image value per segment. The difference between this approximate image and the actual image can be the fit. Select the optimal number of segments based on the fit by determining the minimal number of segments n where the fit still decreases significantly.
When the selected number of segments is larger than two, identifying the middle segment(s) as the segment(s) of the throat wall (when it is equal to or smaller than two, the method should be repeated);
determine the surface area of the identified throat wall segment(s); The surface area of the identified throat wall segments, can for instance be used as a parameter in order to determine whether a patient is suffering from sleep apnea.

In another embodiment, according to a second family, the reflected patterns are not enhanced. The pattern or patterns are used as a basis for accurate depth calculation.

A brief overview of such methods for depth calculation is for instance given in "Pattern codification strategies in structured light systems", J. Salvi et al., Pattern Recognition, vol. 37, page 827-849. 6, 47, April 2004.

Figure 4:
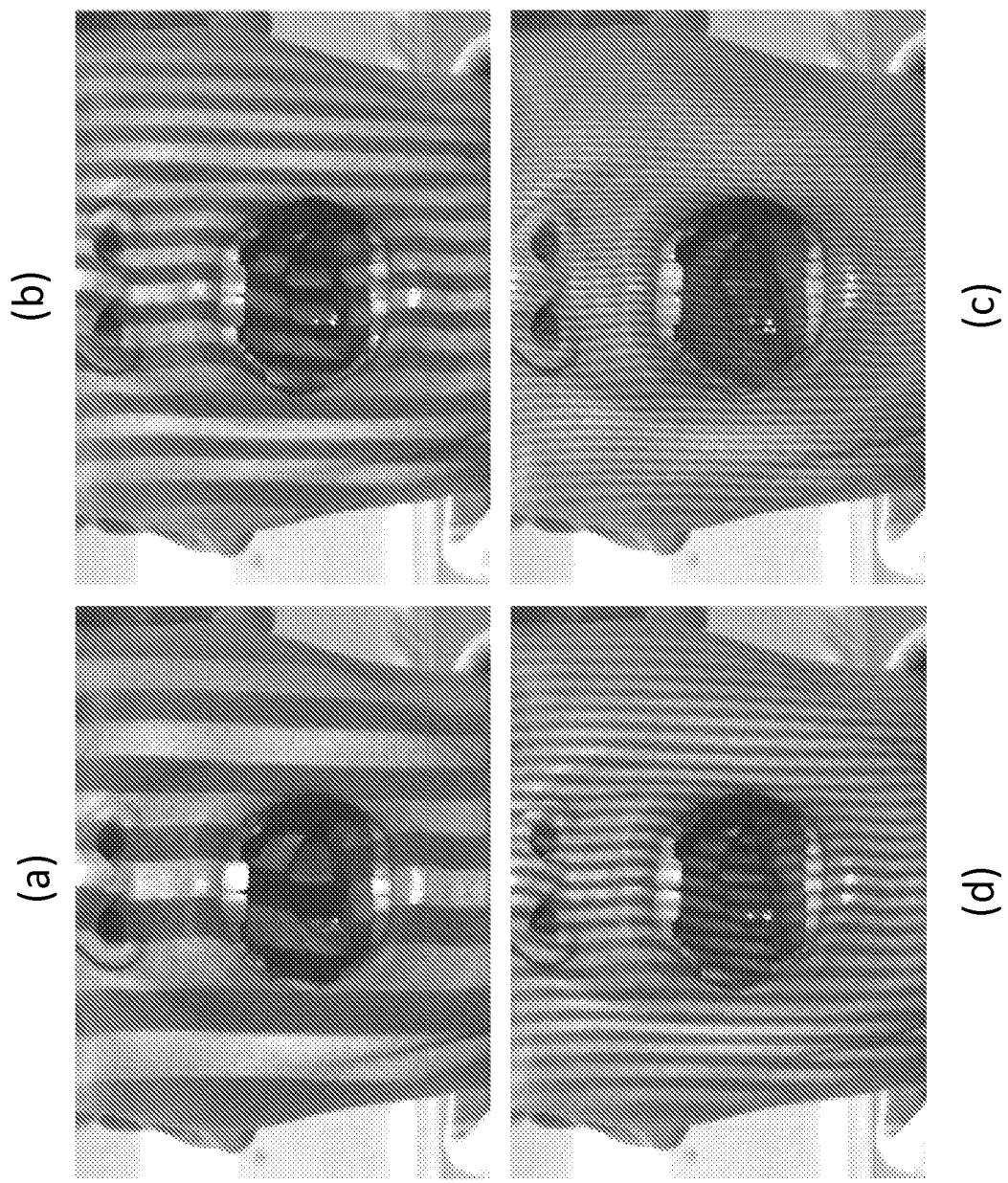
FIG. 4 illustrates an embodiment of the present invention wherein textured illumination is performed with a sequence of different stripe patterns (a), (b), (c), (d).
Figure 5:
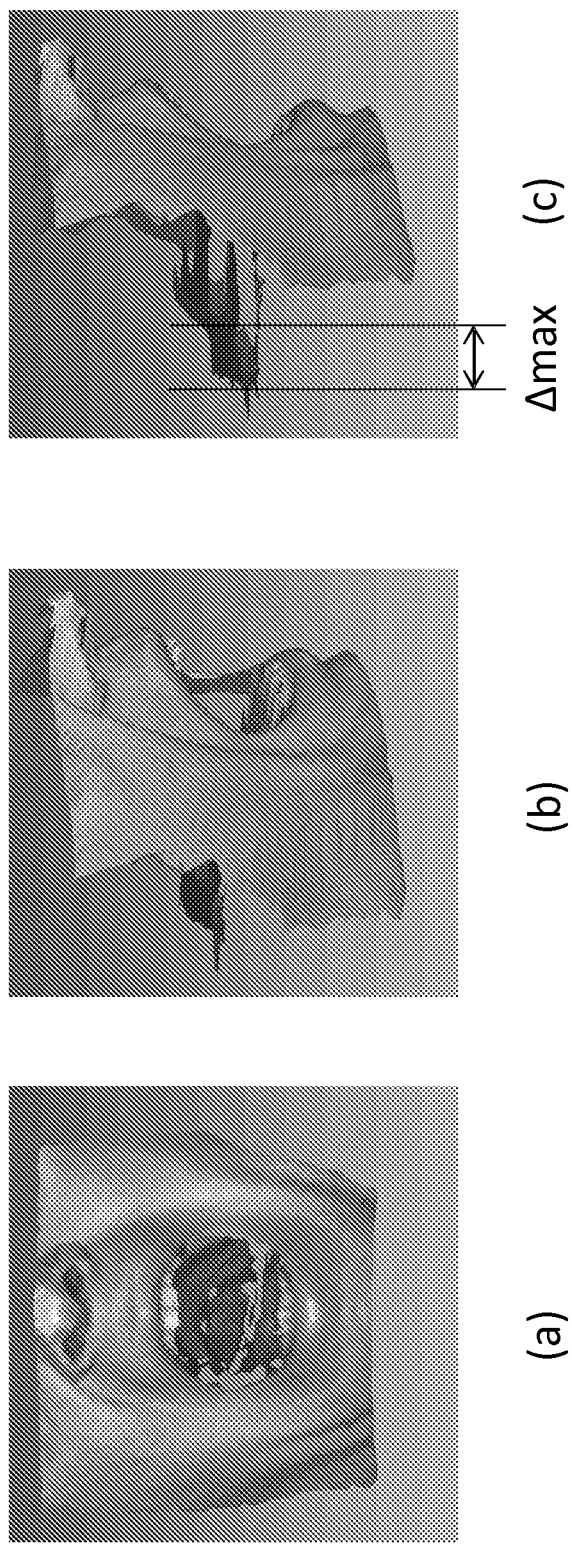
FIG. 5 illustrates a 3D surface, reconstructed on the basis of structured illumination depicted in FIG. 4 (on the basis of 12 patterns); when rendered under different orientations the shape and dimensions of the mouth cavity is revealed.
Figure 6:
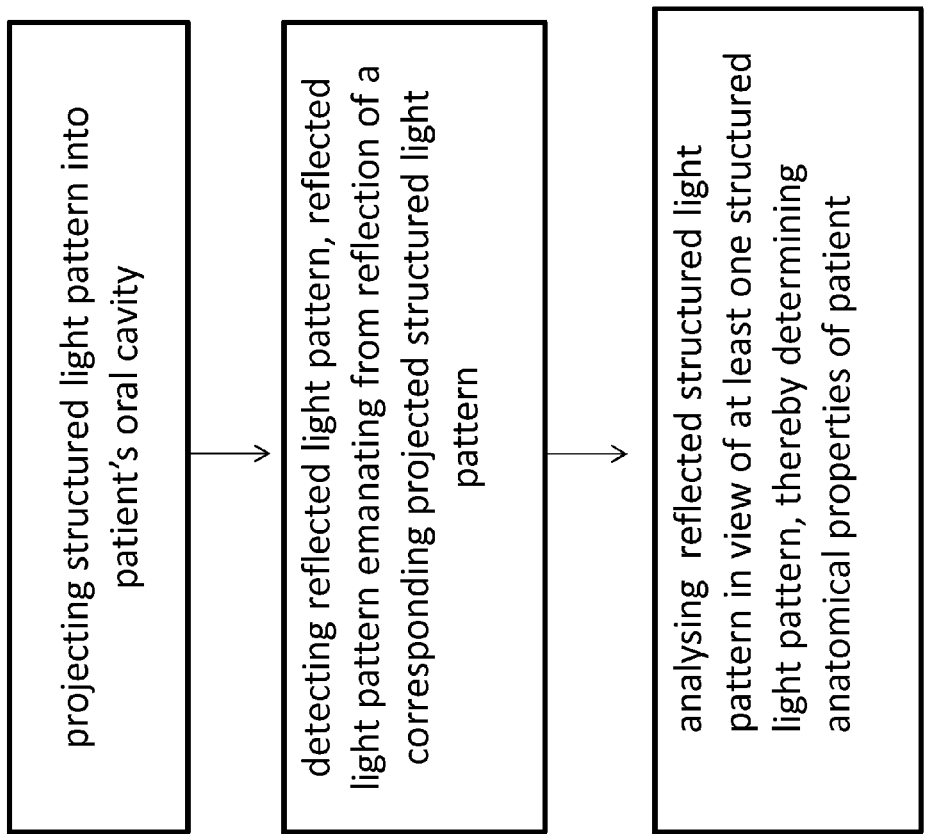
FIG. 6 is a flow chart diagram illustrating the method according to aspects of the present invention.

Some of the acquired images (only a subset of in total twelve captured images is shown) as well as the resulting reconstruction (by rendering under different orientations revealing the shape and dimensions of the mouth cavity) are depicted in FIG. 4 and FIG. 5 respectively. The images have been taken with a relatively large baseline between projector and camera as the system is intended for face capture at a distance of about a meter. For the application to throat imaging, a system can easily have a baseline of less than 7 cm, less than 5 cm, less than 4 cm, or less than 3 cm, or less than 2.5 cm, or less than 2 cm, or less than 1 cm, or less, as the proximity to the opened mouth is much smaller. Note that also here the use of one or more polarisation filters in front of the projector and camera would suppress the specular reflections due to saliva. When the filters have opposite polarisation modes (e.g. projector horizontal and camera vertical, or projector left circular and camera right circular), specular reflections can be attenuated.

The depth image allows for the calculation of the saggital diameter of the velopharynx (see FIG. 2). As before, the throat area can be detected and segmented, however, now including depth information. Using knowledge of the expected typical value for the depth from the mouth up to the velum (or: soft palate) correct execution of the measurement (camera position and orientation, mouth sufficiently opened) can be verified. The system can advise to repeat the measurement if needed. Subsequently, the depth saggital diameter Ds is derived as the distance $\Delta$max, or based on the distance $\Delta$max, between the two most remote segments, see FIG. 5.

According to preferred embodiment, the method also comprises the use of a (preferably replaceable, even more preferably disposable) spatula for depressing the tongue while performing the projection and imaging. An advantage of the spatula is that method can be performed in a substantially reproducible way, because the imaging device can be positioned in a substantially reproducible way. Without the use of a spatula, the tongue may otherwise block the relevant elements in the mouth from being captured with the camera. The spatula can push the tongue out of the imaging system so that it is not in the way. Another advantage is that the imaging system can be used in more or less the same angle/distance for different patients; the tongue's location is not substantially variable. Otherwise the physician would have to align the imaging system every time and for every patient again since the tongue can be in different locations.

According to preferred embodiments, the information derived through any of the above procedures can be combined with other features which are known to be indicative for sleep apnea, as for instance Body Mass Index and gender, or an optical measurement of facial features for Continuous Pressure Airway Pressure mask fitting (It is known that these facial features by themselves are at the same time additional indicators for Obstructive Sleep Apnea), to get the best screening performance.

According to preferred embodiments, this invention can also be used in combination with pharyngeal endoscopy, i.e. including the projection and detection of the light patterns to an endoscope, and to perform the corresponding calculations to derive information about anatomical features. While being more obtrusive, this approach can also deliver more accurate and more detailed information, in particular for those parts of the pharynx not visible from outside the mouth.

Embodiments of the invention can be applied for OSA screening, but can also be used for instance for:

OSA phenotyping. 3D features of the mouth and tongue help to identify different types of OSA, providing an indication for the most successful treatment (CPAP, surgery).

Respiratory drug delivery systems. Knowledge of the anatomical properties of the oral cavity/throat can improve the proportion of the administered drug that needs to be delivered to a desired location.

It is to be understood that although preferred embodiments, specific constructions and configurations, as well as materials, have been discussed herein for devices according to the present invention, various changes or modifications in form and detail may be made without departing from the scope of this invention.

The invention claimed is:

1. A method for determining anatomical properties of a patient, said patient having an oral cavity and a throat, comprising:
    a) projecting at least one structured light pattern into said patient's oral cavity;
    b) detecting at least one reflected light pattern, each of said reflected light patterns emanating from reflection of a corresponding projected structured light pattern;
    c) analysing said at least one reflected structured light pattern in view of said at least one structured light pattern, thereby determining anatomical properties of said patient;
        wherein each of said at least one structured light pattern comprises a set of predetermined parallel lines of projected light and is such that said set of predetermined parallel lines of projected light defines a structure comprising an area of higher projected light line density and an area lower projected light line density areas and/or comprising an area of larger projected light line thickness and an area of smaller projected light line thickness, the projections thereof corresponding with predetermined locations in said oral cavity and throat, further comprising polarising said structured light patterns before reflection, according to a first polarisation mode, and polarising said reflected light patterns before detection, according to a second polarisation mode, said first and second polarisation modes being opposite.

2. A method according to claim 1, wherein a baseline between the position of projecting at least one structured light pattern and the position of detecting at least one reflected light pattern, is smaller than 7 cm.

3. A method according to claim 1, wherein said patient comprises a tongue, the method further comprising depressing said tongue while performing (a).

4. A method according to claim 1, wherein (b) comprises making one or more photographic image of said patient's oral cavity.

5. A method according to claim 4, further comprising making at least one photographic reference image of said patient's oral cavity, and wherein (c) further comprises subtracting said photographic reference image(s) from said respective photographic image(s) made in (b).

6. A method according to claim 1, further comprising detecting fractures in reflected lines of reflected light patterns, and associating said fractures with boundaries of anatomic features of said oral cavity.

7. A method according to claim 1, further comprising detecting deformation of reflected lines of reflected light patterns detected in (b), and associating said deformation with shape information of anatomic features of said oral cavity.

8. A method according to claim 1, wherein said anatomical properties of said patient comprise an extent to which the back of said throat is occluded by other anatomical features forming the oral cavity or within the oral cavity.

9. A method according to claim 1, wherein said anatomical properties of said patient comprise depth information for anatomic features within said oral cavity or throat.

10. An imaging device for determining anatomical properties of a patient, said patient having an oral cavity and a throat, comprising
    a. a means for projecting at least one structured light pattern into said patient's oral cavity;
    b. a means for detecting at least one reflected light pattern, each of said reflected light patterns emanating from reflection of a corresponding projected structured light pattern;
    c. a means for analysing said at least one reflected structured light pattern in view of said at least one structured light pattern, thereby determining anatomical properties of said patient;
        wherein each of said at least one structured light pattern comprises a set of predetermined parallel lines of projected light and is such that said set of predetermined parallel lines defines a structure comprising an area of higher projected light line density and an area of lower projected light line density and/or comprising an area of larger projected light line thickness and an area of projected light smaller line thickness, the projections thereof corresponding with predetermined locations in said oral cavity and throat;
        further comprising a first polarization means structured to polarize said at least one structured light pattern according to a first polarization mode before being projected into said patient's oral cavity, and a second polarization means structured to polarize said at least one reflected light pattern before being detected by said means for detecting according to a second polarization mode, wherein said first and second polarization modes are opposite.

11. An imaging device for determining anatomical properties of a patient, said patient having an oral cavity and a throat, comprising
    a. a projector for projecting at least one structured light pattern into said patient's oral cavity;
    b. an imaging device for detecting at least one reflected light pattern, each of said reflected light patterns emanating from reflection of a corresponding projected structured light pattern;
    c. a computer comprising software for analysing said at least one reflected structured light pattern in view of said at least one structured light pattern, thereby determining anatomical properties of said patient;
        wherein each of said at least one structured light pattern comprises a set of predetermined parallel lines of projected light and is such that said set of predetermined parallel lines defines a structure comprising an area of higher projected light line density and an area of lower projected light line density and/or comprising an area of larger projected light line thickness and an area of projected light smaller line thickness, the projections thereof corresponding with predetermined locations in said oral cavity and throat;

further comprising a first polarization filter structured to polarize said at least one structured light pattern according to a first polarization mode before being projected into said patient's oral cavity, and a second polarization filter structured to polarize said at least one reflected light pattern before being detected by said imaging device according to a second polarization mode, wherein said first and second polarization modes are opposite.

12. An imaging device for determining anatomical properties of a patient, said patient having an oral cavity and a throat, comprising
   a. a projector for projecting at least one structured light pattern into said patient's oral cavity;
   b. an imaging device for detecting at least one reflected light pattern, each of said reflected light patterns emanating from reflection of a corresponding projected structured light pattern;
   c. a computer comprising software for analysing said at least one reflected structured light pattern in view of said at least one structured light pattern, thereby determining anatomical properties of said patient;
   wherein each of said at least one structured light pattern comprises a set of predetermined parallel lines of projected light and is such that said set of predetermined parallel lines defines a structure comprising an area of higher projected light line density and an area of lower projected light line density and/or comprising an area of larger projected light line thickness and an area of projected light smaller line thickness, the projections thereof corresponding with predetermined locations in said oral cavity and throat, wherein the analysing comprises detecting fractures in reflected lines of reflected light patterns, and associating said fractures with boundaries of anatomic features of said oral cavity.

13. An imaging device for determining anatomical properties of a patient, said patient having an oral cavity and a throat, comprising
   a. a projector for projecting at least one structured light pattern into said patient's oral cavity;
   b. an imaging device for detecting at least one reflected light pattern, each of said reflected light patterns emanating from reflection of a corresponding projected structured light pattern;
   c. a computer comprising software for analysing said at least one reflected structured light pattern in view of said at least one structured light pattern, thereby determining anatomical properties of said patient;
   wherein each of said at least one structured light pattern comprises a set of predetermined parallel lines of projected light and is such that said set of predetermined parallel lines defines a structure comprising an area of higher projected light line density and an area of lower projected light line density and/or comprising an area of larger projected light line thickness and an area of projected light smaller line thickness, the projections thereof corresponding with predetermined locations in said oral cavity and throat, wherein the analysing comprises detecting deformation of reflected lines of reflected light patterns detected in (b), and associating said deformation with shape information of anatomic features of said oral cavity.

* * * * *